(12) United States Patent
Kostansek et al.

(10) Patent No.: US 8,691,728 B2
(45) Date of Patent: Apr. 8, 2014

(54) CYCLOPROPENE COMPOSITIONS

(75) Inventors: Edward Charles Kostansek, Buckingham, PA (US); Bridget Marie Stevens, Horsham, PA (US)

(73) Assignee: Rohm and Haas Company, Indianapolis, IN (US)

( * ) Notice: Subject to any disclaimer, the term of this patent is extended or adjusted under 35 U.S.C. 154(b) by 1224 days.

(21) Appl. No.: 11/975,323

(22) Filed: Oct. 18, 2007

(65) Prior Publication Data

US 2008/0113867 A1 May 15, 2008

Related U.S. Application Data

(60) Provisional application No. 60/858,253, filed on Nov. 9, 2006.

(51) Int. Cl.
| | |
|---|---|
| A01N 27/00 | (2006.01) |
| A01N 3/02 | (2006.01) |
| A01N 25/28 | (2006.01) |
| A01N 37/00 | (2006.01) |
| A01N 29/00 | (2006.01) |
| A01N 31/00 | (2006.01) |
| A01N 33/00 | (2006.01) |
| C07C 2/02 | (2006.01) |
| C07C 5/31 | (2006.01) |
| C07C 5/32 | (2006.01) |
| C07C 13/00 | (2006.01) |

(52) U.S. Cl.
USPC ........... 504/357; 504/114; 504/115; 504/320; 504/326; 504/353; 504/356; 504/359; 585/23; 585/365; 585/379; 585/506

(58) Field of Classification Search
USPC ......... 504/357, 114, 115, 320, 326, 353, 356, 504/359; 585/23, 365, 379, 506
See application file for complete search history.

(56) References Cited

U.S. PATENT DOCUMENTS

| | | | |
|---|---|---|---|
| 5,371,209 A * | 12/1994 | Shieh et al. | 560/103 |
| 6,017,849 A | 1/2000 | Daly | |
| 6,313,068 B1 | 11/2001 | Daly | |
| 6,426,319 B1 | 7/2002 | Kostansek | |
| 6,762,153 B2 * | 7/2004 | Kostansek et al. | 504/357 |
| 2005/0261132 A1 | 11/2005 | Kostansek et al. | |

FOREIGN PATENT DOCUMENTS

| | | |
|---|---|---|
| CN | 1505992 | 6/2004 |
| EP | 1192858 | 4/2002 |
| EP | 1304035 | 4/2003 |
| EP | 1602276 | 12/2005 |
| WO | WO 0224171 | 3/2002 |

OTHER PUBLICATIONS

Schneider et al., "Solvent and Salt Effects on Binding Constants of Organic Substrates in Macrocyclic Host Compounds. A General Equation Measuring Hydrophobic Binding Contributions," 1988, J. Am. Chem. Soc., 110:6442-6448.*
Kotake et al., "Effect of pH and Salt Concentrations on Bimodal Inclusion of a Nitroxide by Cyclodextrins," 1989, J. Am. Chem. Soc., 111:7319-7323.*
Schneider, H-J, et. al., "Solvent and salt effects on binding constants of organic substrates . . . ", Journal of the American Chemical Association, v. 110, p. 6442-6448, 1988.
Kotake, Y., et al, "Effect of pH and salt concentration on bimodal inclusion of a nitroxide . . . ," Journal of the American Chemical Association, v. 111, pp. 7319-7323, 1989.
Schienk, H, et al, "Association of alpha- and beta-cyclodextrins with organic acids," Journal of the American Chemical Association, v. 83, pp. 2312-2320, 1960.

* cited by examiner

*Primary Examiner* — Jane C Oswecki
(74) *Attorney, Agent, or Firm* — Yung H. Lee

(57) ABSTRACT

Provided is a composition comprising
  (a) at least one cyclopropene molecular encapsulating agent complex, and
  (b) at least one salt other than calcium chloride,
wherein the ratio of dry weight of said salt to dry weight of said cyclopropene molecular encapsulating agent complex is from 0.03 to 500, and wherein said composition either
  (i) has 30% or less water by weight, based on the weight of said composition, and has at least one said salt that is non-deliquescent, or
  (ii) has more than 30% water by weight, based on the weight of said composition, and has a ratio of dry weight of said salt to weight of said water of 0.05 or higher.
Also provided are methods of storing and using such compositions.

3 Claims, No Drawings

CYCLOPROPENE COMPOSITIONS

This application claims the benefit of priority under 35 U.S.C. §119(e) of U.S. Provisional Patent Application No. 60/858,253 filed on Nov. 9, 2006.

BACKGROUND

Cyclopropene compounds are useful for treating plants or plant parts. As a way of storing cyclopropenes or of delivering them to plant parts, or both, it is sometimes useful to form complexes of cyclopropene molecules with molecular complexing agents. In the past, it has been considered that contact between such complexes and water will quickly release cyclopropene molecules from the complex. Also, in the past, it has been observed that when such complexes are mixed with water, some or all of the cyclopropene disappears, possibly because one or more chemical reaction turns the cyclopropene into a different compound.

U.S. Pat. No. 6,426,319 discloses methods of releasing cyclopropene from a complex of cyclopropene and molecular encapsulation agent. The methods of U.S. Pat. No. 6,426,319 involve the use of a composition comprising a cyclopropene encapsulated in a molecular encapsulating agent and a water absorbent material, which may be, for example, an inorganic deliquescent compound. In the methods of U.S. Pat. No. 6,426,319, when such complexes are exposed to water or to an atmosphere with high humidity, cyclopropene is released into the atmosphere.

It is desired to provide compositions that contain cyclopropene; that contain water; and that have one or both of these benefits: (A) retardation or prevention of the degradation of cyclopropene during storage and/or during processing, or (B) retardation or prevention of the release of cyclopropene to the atmosphere. It is also desired to provide compositions that contain cyclopropene and that can be added to water to form water-containing compositions that have one or both of the same benefits (A) or (B) defined above.

STATEMENT OF THE INVENTION

In a first aspect of the present invention, there is provided a composition comprising
 (a) at least one cyclopropene molecular encapsulating agent complex, and
 (b) at least one salt other than calcium chloride,
 wherein the ratio of dry weight of said salt to dry weight of said cyclopropene molecular encapsulating agent complex is from 0.03 to 500, and wherein said composition either
 (i) has 30% or less water by weight, based on the weight of said composition, and has at least one said salt that is non-deliquescent, or
 (ii) has more than 30% water by weight, based on the weight of said composition, and has a ratio of dry weight of said salt to weight of said water of 0.05 or higher.

DETAILED DESCRIPTION

The practice of the present invention involves the use of one or more cyclopropenes. As used herein, "a cyclopropene" is any compound with the formula

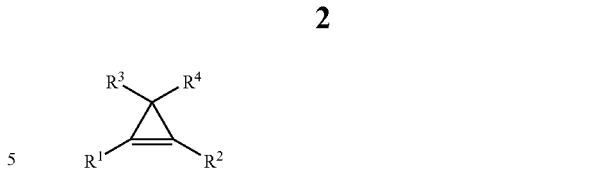

where each $R^1$, $R^2$, $R^3$ and $R^4$ is independently selected from the group consisting of H and a chemical group of the formula:

$$-(L)_n-Z$$

where n is an integer from 0 to 12. Each -L- is a bivalent radical. Suitable L groups include, for example, radicals containing one or more atoms selected from B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

Among embodiments in which at least one of $R^1$, $R^2$, $R^3$, and $R^4$ is not hydrogen and has more than one L group, the L groups within that particular $R^1$, $R^2$, $R^3$, or $R^4$ group may be the same as the other L groups within that same $R^1$, $R^2$, $R^3$, or $R^4$ group, or any number of L groups within that particular $R^1$, $R^2$, $R^3$, or $R^4$ group may be different from the other L groups within that same $R^1$, $R^2$, $R^3$, or $R^4$ group.

Among embodiments in which at least one of $R^1$, $R^2$, $R^3$, and $R^4$ contains more than one Z group, the Z groups within that $R^1$, $R^2$, $R^3$, or $R^4$ group may be the same as the other Z groups within that $R^1$, $R^2$, $R^3$, or $R^4$ group, or any number of Z groups within that $R^1$, $R^2$, $R^3$, or $R^4$ group may be different from the other Z groups within that $R^1$, $R^2$, $R^3$, or $R^4$ group.

The $R^1$, $R^2$, $R^3$, and $R^4$ groups are independently selected from the suitable groups. The $R^1$, $R^2$, $R^3$, and $R^4$ groups may be the same as each other, or any number of them may be different from the others. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted. Independently, groups that are suitable for use as one or more of $R^1$, $R^2$, $R^3$, and $R^4$ may be connected directly to the cyclopropene ring or may be connected to the cyclopropene ring through an intervening group such as, for example, a heteroatom-containing group.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atom of the chemical group of interest is replaced by a substituent. It is contemplated that such substituted groups may be made by any method, including but not limited to making the unsubstituted form of the chemical group of interest and then performing a substitution. Suitable substituents include, for example, alkyl, alkenyl, acetylamino, alkoxy, alkoxyalkoxy, alkoxycarbonyl, alkoxyimino, carboxy, halo, haloalkoxy, hydroxy, alkylsulfonyl, alkylthio, trialkylsilyl, dialkylamino, and combinations thereof. An additional suitable substituent, which, if present, may be present alone or in combination with another suitable substituent, is -(L)$_m$-Z, where m is 0 to 8, and where L and Z are defined herein above. If more than one substituent is present on a single chemical group of interest, each substituent may replace a different hydrogen atom, or one substituent may be attached to another substituent, which in turn is attached to the chemical group of interest, or a combination thereof.

Among the suitable $R^1$, $R^2$, $R^3$, and $R^4$ groups are, for example, substituted and unsubstituted aliphatic-oxy groups, such as, for example, alkenoxy, alkoxy, alkynoxy, and alkoxycarbonyloxy.

Also among the suitable $R^1$, $R^2$, $R^3$, and $R^4$ groups are, for example, substituted and unsubstituted alkylphosphonato, substituted and unsubstituted alkylphosphato, substituted and unsubstituted alkylamino, substituted and unsubstituted alkylsulfonyl, substituted and unsubstituted alkylcarbonyl, and substituted and unsubstituted alkylaminosulfonyl, including, for example, alkylphosphonato, dialkylphosphato, dialkylthiophosphato, dialkylamino, alkylcarbonyl, and dialkylaminosulfonyl.

Also among the suitable $R^1$, $R^2$, $R^3$, and $R^4$ groups are, for example, substituted and unsubstituted cycloalkylsulfonyl groups and cycloalkylamino groups, such as, for example, dicycloalkylaminosulfonyl and dicycloalkylamino.

Also among the suitable $R^1$, $R^2$, $R^3$, and $R^4$ groups are, for example, substituted and unsubstituted heterocyclyl groups (i.e., non-aromatic cyclic groups with at least one heteroatom in the ring).

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted aryl groups, and substituted and unsubstituted heteroaryl groups. Suitable substituents are those described herein above. In some embodiments, one or more substituted aryl or heteroaryl group is used in which at least one substituent is one or more of alkenyl, alkyl, alkynyl, acetylamino, oxy, alkoxyalkoxy, alkoxy, alkoxycarbonyl, carbonyl, alkylcarbonyloxy, carboxy, arylamino, haloalkoxy, halo, hydroxy, trialkylsilyl, dialkylamino, alkylsulfonyl, sulfonylalkyl, alkylthio, thioalkyl, arylaminosulfonyl, and haloalkylthio.

Also among the suitable $R^1$, $R^2$, $R^3$, and $R^4$ groups are, for example, substituted and unsubstituted heteroaryl groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated 3 membered ring, such as, for example, a substituted or unsubstituted cyclopropane, cyclopropene, epoxide, or aziridine ring.

In some embodiments, G is a ring system that contains a 4 membered heterocyclic ring; in some of such embodiments, the heterocyclic ring contains exactly one heteroatom. Independently, in some embodiments, G is a ring system that contains a heterocyclic ring with 5 or more members; in some of such embodiments, the heterocyclic ring contains 1 to 4 heteroatoms. Independently, in some embodiments, the ring in G is unsubstituted; in other embodiments, the ring system contains 1 to 5 substituents; in some of the embodiments in which G contains substituents, each substituent is independently chosen from the substituents described herein above. Also suitable are embodiments in which G is a carbocyclic ring system.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments include those embodiments, for example, in which G is unsubstituted or substituted phenyl, cyclopentyl, cycloheptyl, or cyclohexyl. In some of these embodiments, G is cyclopentyl, cycloheptyl, cyclohexyl, phenyl, or substituted phenyl. Among embodiments in which G is substituted phenyl are embodiments, for example, in which there are 1, 2, or 3 substituents. Independently, also among embodiments in which G is substituted phenyl are embodiments, for example, in which the substituents are independently selected from methyl, methoxy, and halo.

Also contemplated are embodiments in which $R^3$ and $R^4$ are combined into a single group, which is attached to the number 3 carbon atom of the cyclopropene ring by a double bond. Some of such compounds are described in US Patent Publication 2005/0288189.

In some embodiments, one or more cyclopropenes are used in which one or more of $R^1$, $R^2$, $R^3$, and $R^4$ is hydrogen. In some embodiments, $R^1$ or $R^2$ or both $R^1$ and $R^2$ is hydrogen. Independently, in some embodiments, $R^3$ or $R^4$ or both $R^3$ and $R^4$ is hydrogen. In some embodiments, $R^2$, $R^3$, and $R^4$ are hydrogen.

In some embodiments, one or more of $R^1$, $R^2$, $R^3$, and $R^4$ is a structure that has no double bond. Independently, in some embodiments, one or more of $R^1$, $R^2$, $R^3$, and $R^4$ is a structure that has no triple bond. Independently, in some embodiments, one or more of $R^1$, $R^2$, $R^3$, and $R^4$ is a structure that has no halogen atom substituent. Independently, in some embodiments, one or more of $R^1$, $R^2$, $R^3$, and $R^4$ is a structure that has no substituent that is ionic. Independently, in some embodiments, one or more of $R^1$, $R^2$, $R^3$, and $R^4$ is a structure that is not capable of generating oxygen compounds.

In some embodiments of the invention, one or more of $R^1$, $R^2$, $R^3$, and $R^4$ is hydrogen or ($C_1$-$C_{10}$) alkyl. In some embodiments, each of $R^1$, $R^2$, $R^3$, and $R^4$ is hydrogen or ($C_1$-$C_8$) alkyl. In some embodiments, each of $R^1$, $R^2$, $R^3$, and $R^4$ is hydrogen or ($C_1$-$C_4$) alkyl. In some embodiments, each of $R^1$, $R^2$, $R^3$, and $R^4$ is hydrogen or methyl. In some embodiments, $R^1$ is ($C_1$-$C_4$) alkyl and each of $R^2$, $R^3$, and $R^4$ is hydrogen. In some embodiments, $R^1$ is methyl and each of $R^2$, $R^3$, and $R^4$ is hydrogen, and the cyclopropene is known herein as "1-MCP."

In some embodiments, a cyclopropene is used that has boiling point at one atmosphere pressure of 50° C. or lower; or 25° C. or lower; or 15° C. or lower. Independently, in some embodiments, a cyclopropene is used that has boiling point at one atmosphere pressure of −100° C. or higher; −50° C. or higher; or −25° C. or higher; or 0° C. or higher.

The cyclopropenes applicable to this invention may be prepared by any method. Some suitable methods of preparation of cyclopropenes are the processes disclosed in U.S. Pat. Nos. 5,518,988 and 6,017,849.

The composition of the present invention includes at least one molecular encapsulating agent. In some embodiments, at least one molecular encapsulating agent encapsulates one or more cyclopropene or a portion of one or more cyclopropene. A complex that contains a cyclopropene molecule or a portion of a cyclopropene molecule encapsulated in a molecule of a molecular encapsulating agent is known herein as a "cyclopropene molecular encapsulating agent complex."

In some embodiments, at least one cyclopropene molecular encapsulating agent complex is present that is an inclusion complex. In such an inclusion complex, the molecular encapsulating agent forms a cavity, and the cyclopropene or a portion of the cyclopropene is located within that cavity. In some of such inclusion complexes, there is no covalent bonding between the cyclopropene and the molecular encapsulating agent. Independently, in some of such inclusion complexes, there is no ionic bonding between the cyclopropene and the molecular encapsulating complex, whether or not there is any electrostatic attraction between one or more polar moiety in the cyclopropene and one or more polar moiety in the molecular encapsulating agent.

Independently, in some of such inclusion complexes, the interior of the cavity of the molecular encapsulating agent is substantially apolar or hydrophobic or both, and the cyclopropene (or the portion of the cyclopropene located within that cavity) is also substantially apolar or hydrophobic or both. While the present invention is not limited to any particular theory or mechanism, it is contemplated that, in such apolar cyclopropene molecular encapsulating agent complexes, van der Waals forces, or hydrophobic interactions, or both, cause the cyclopropene molecule or portion thereof to remain within the cavity of the molecular encapsulating agent.

The cyclopropene molecular encapsulation agent complexes can be prepared by any means. In one method of preparation, for example, such complexes are prepared by contacting the cyclopropene with a solution or slurry of the molecular encapsulation agent and then isolating the complex, using, for example, processes disclosed in U.S. Pat. No. 6,017,849. For example, in one method of making a complex in which 1-MCP is encapsulated in a molecular encapsulating agent, the 1-MCP gas is bubbled through a solution of alpha-cyclodextrin in water, from which the complex first precipitates and is then isolated by filtration. In some embodiments, complexes are made by the above method and, after isolation, are dried and stored in solid form, for example as a powder, for later addition to useful compositions.

The amount of molecular encapsulating agent can usefully be characterized by the ratio of moles of molecular encapsulating agent to moles of cyclopropene. In some embodiments, the ratio of moles of molecular encapsulating agent to moles of cyclopropene is 0.1 or larger; or 0.2 or larger; or 0.5 or larger; or 0.9 or larger. Independently, in some of such embodiments, the ratio of moles of molecular encapsulating agent to moles of cyclopropene is 2 or lower; or 1.5 or lower.

Suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments of the invention, the encapsulating agent is alpha-cyclodextrin, beta-cyclodextrin, gamma-cyclodextrin, or a mixture thereof. In some embodiments of the invention, alpha-cyclodextrin is used. The preferred encapsulating agent will vary depending upon the structure of the cyclopropene or cyclopropenes being used. Any cyclodextrin or mixture of cyclodextrins, cyclodextrin polymers, modified cyclodextrins, or mixtures thereof can also be utilized pursuant to the present invention. Some cyclodextrins are available, for example, from Wacker Biochem Inc., Adrian, Mich. or Cerestar USA, Hammond, Ind. as well as other vendors.

The practice of the present invention involves the use of at least one salt other than calcium chloride. As used herein, a salt is an ionic compound comprising at least one anion and at least one cation. A salt may be present as an ionic solid or as a solution in water. Some suitable anions are, for example, the anion residues of acids that have pKa values of 5 or lower. Some suitable salts, for example, are compounds that, regardless of the method used to actually make them, have the structure of a compound that would be formed by substituting a cation that is not a hydrogen ion for the hydrogen ion in an acid that has a pKa of 5 or lower; or an acid that has a pKa of 2.5 or lower; or an acid that has a pKa of 0 or lower.

In some embodiments, one or more salt is used that is suitable for treating agricultural plants. Independently, in some embodiments, one or more salt is used that has solubility in water at 25° C., at 1 atmosphere pressure, per 100 ml of water, of 1 gram or more, or 3 grams or more, or 10 grams or more, or 20 grams or more, or 30 grams or more.

Some non-limiting examples of suitable anions are these: acetate, chloride, nitrate, phosphate, or sulfate. Independently, some non-limiting examples of suitable cations are these: ammonium, calcium, magnesium, manganese, potassium, or sodium. It is contemplated that suitable cations and suitable anions may be used in any combination or mixture, with the provision that at least one salt is used that is not calcium chloride.

In some embodiments, no appreciable amount of calcium chloride is present in the composition of the present invention. It is contemplated that a finite but non-appreciable amount of calcium chloride may be present in a composition of the present invention (for example, because of one or more impurities). Calcium chloride may be present with a ratio of dry weight of calcium chloride to dry weight of total salt of 0.03 or less; or 0.01 or less; or 0.003 or less; or 0.001 or less; or zero.

In some embodiments, one or more salt is used that is selected from ammonium acetate, ammonium chloride, ammonium nitrate, ammonium phosphate, ammonium sulfate, calcium acetate, magnesium acetate, magnesium chloride, magnesium sulfate, manganese nitrate, potassium acetate, potassium chloride, potassium phosphate, potassium sulfate, sodium acetate, sodium chloride, sodium phosphate, or sodium sulfate. In some embodiments, one or more salt is used that is selected from ammonium acetate, ammonium chloride, ammonium sulfate, magnesium acetate, magnesium chloride, magnesium sulfate, potassium acetate, potassium chloride, potassium phosphate, sodium acetate, sodium chloride, disodium phosphate, or sodium sulfate. In some embodiments, one or more salt is used that is selected from ammonium chloride, ammonium sulfate, magnesium sulfate, sodium acetate, sodium chloride, disodium phosphate, or sodium sulfate. Mixtures of suitable salts are also suitable.

In some embodiments, one or more sulfate salt is used. Independently, in some embodiments, no chloride salt is used.

In compositions of the present invention, the ratio of the dry weight of salt to the dry weight of cyclopropene molecular encapsulating agent complex is 0.03 or higher; or 0.1 or higher; or 0.3 or higher; or 1 or higher. Independently, in compositions of the present invention, the ratio of the dry weight of salt to the dry weight of cyclopropene molecular encapsulating agent complex is 500 or lower; or 200 or lower; or 100 or lower; or 50 or lower; or 20 or lower.

In some embodiments, the composition of the present invention contains more than 30% water by weight, based on the weight of the composition. Such embodiments are known herein as "relatively wet" embodiments. Some relatively wet embodiments have water in an amount, by weight based on the weight of the composition, of 50% or more; or 60% or more.

In relatively wet embodiments, the ratio of the dry weight of salt to the weight of water is 0.05 or higher; or 0.1 or higher; or 0.2 or higher; or 0.3 or higher; or 0.35 or higher. Independently, in some relatively wet embodiments, the ratio of the dry weight of salt to the weight of water is 0.6 or lower; or 0.5 or lower.

In some relatively wet embodiments, the ratio of the dry weight of cyclopropene molecular encapsulating complex to the sum of the weight of water and the weight of salt is 0.005 or higher; or 0.01 or higher; or 0.02 or higher; or 0.05 or higher; or 0.1 or higher; or 0.2 or higher. Independently, in some relatively wet embodiments, the ratio of the dry weight of cyclopropene molecular encapsulating complex to the sum of the weight of water and the weight of salt is 0.65 or lower; or 0.45 or lower; or 0.3 or lower.

In some relatively wet embodiments, at least one cyclopropene molecular encapsulating complex is distributed throughout the water. Independently, in some relatively wet embodiments, at least one salt is dissolved in the water.

Also contemplated are embodiments in which the composition of the present invention is present in a formulation that contains more than 30% by weight, based on the weight of the formulation, a liquid that contains at least one compound other than water. Such a liquid may have no water. In some embodiments, such a liquid may be a mixture of water and one or more water miscible liquids other than water. In such a mixture, the amount of water, by weight based on the weight of the liquid, may be 99% or less; or 95% or less; 90% or less; or 50% or less; or 10% or less. Independently, in such a mixture, the amount of water, by weight based on the weight of the liquid, may be 5% or more; or 45% or more; or 75% or more.

In some embodiments, the composition of the present invention is relatively dry, and may be in a form such as, for example, a powder, a paste, or pellets. As used herein, a relatively dry embodiment is a composition of the present invention that contains 30% water or less by weight, based on the weight of the composition. Some relatively dry embodiments have water in the amount, by weight based on the weight of the composition, of 30% or less; or 10% or less; or 3% or less; or 1% or less. Some relatively dry embodiments may optionally contain one or more further ingredients, such as, for example, binders or flow aids.

In the practice of the present invention, relatively dry embodiments of the present invention contain at least one non-deliquescent salt. A non-deliquescent salt is a salt that is not a deliquescent salt. A deliquescent salt is a salt that, in its solid form, readily absorbs large amounts of water from the atmosphere. At 25° C. and 1 atmosphere pressure, if relative humidity is not zero, a deliquescent salt will absorb sufficient water from the atmosphere to form a liquid solution. Some known deliquescent salts are, for example, ammonium formate; calcium chloride; magnesium chloride; potassium phosphate, monobasic; and potassium phosphate, dibasic. In some embodiments, relatively dry embodiments of the present invention do not contain appreciable amounts of any deliquescent salt. It is contemplated that a finite but non-appreciable amount of deliquescent salt may be present in a relatively dry embodiment of the present invention (for example, because of one or more impurities). Deliquescent salt may be present in a ratio of dry weight of deliquescent salt to dry weight of total salt of 0.01 or lower; or 0.001 or lower; or zero.

A relatively dry embodiment of the present invention, if used, may be made by any method. For example, salt in a relatively dry form (such as, for example, powder or granules) may be mixed with cyclopropene molecular encapsulating agent complex in relatively dry form (such as, for example, powder). For another example, a composition containing more than 30% water may be prepared that contains a salt and a cyclopropene molecular encapsulating agent complex, and the water may be separated from the other ingredients of the composition, for example by drying, filtration, coagulation, or combinations thereof. Some relatively dry embodiments are extruded and, optionally, cut into pellets.

In some relatively dry embodiments, the ratio of the weight of salt to the weight of cyclopropene molecular encapsulating agent complex is 0.01 or greater; or 0.03 or greater; or 0.1 or greater; or 0.3 or greater; or 1 or greater. Independently, in some relatively dry embodiments, the ratio of the weight of salt to the weight of cyclopropene molecular encapsulating agent complex is 200 or less; or 100 or less; or 50 or less; or 20 or less.

Also contemplated are relatively wet embodiments in which no salt is present that is a deliquescent salt, or in which a finite but non-appreciable amount of deliquescent salt (as defined herein above) is present.

In some embodiments, no composition of the present invention includes one or more metal-complexing agents.

In some embodiments, one or more compositions of the present invention includes one or more metal-complexing agents. A metal-complexing agent is a compound that is capable of forming coordinate bonds with metal atoms. Some metal-complexing agents are chelating agents. As used herein, a "chelating agent" is a compound, each molecule of which is capable of forming two or more coordinate bonds with a single metal atom. Some metal-complexing agents form coordinate bonds with metal atoms because the metal-complexing agents contain electron-donor atoms that participate in coordinate bonds with metal atoms. Suitable chelating agents include, for example, organic and inorganic chelating agents. Among the suitable inorganic chelating agents are, for example, phosphorous-containing chelating agents such as, for example, tetrasodium pyrophosphate, sodium tripolyphosphate, and hexametaphosphoric acid. Among the suitable organic chelating agents are those with macrocyclic structures and non-macrocyclic structures. Among the suitable macrocyclic organic chelating agents are, for example, porphine compounds, cyclic polyethers (also called crown ethers), and macrocyclic compounds with both nitrogen and oxygen atoms.

Some suitable organic chelating agents that have non-macrocyclic structures are, for example, aminocarboxylic acids, 1,3-diketones, hydroxycarboxylic acids, polyamines, aminoalcohols, aromatic heterocyclic bases, phenol, aminophenols, oximes, Shiff bases, sulfur compounds, and mixtures thereof. In some embodiments, the chelating agent includes one or more aminocarboxylic acids, one or more hydroxycarboxylic acids, one or more oximes, or a mixture thereof. Some suitable aminocarboxylic acids include, for example, ethylenediaminetetraacetic acid (EDTA), hydroxyethylethylenediaminetriacetic acid (HEDTA), nitrilotriacetic acid (NTA), N-dihydroxyethylglycine (2-HxG), ethylenebis(hydroxyphenylglycine) (EHPG), and mixtures thereof. Some suitable hydroxycarboxylic acids include, for example, tartaric acid, citric acid, gluconic acid, 5-sulfosalicylic acid, and mixtures thereof. Some suitable oximes include, for example, dimethylglyoxime, salicylaldoxime, and mixtures thereof. In some embodiments, EDTA is used.

Some additional suitable chelating agents are polymeric. Some suitable polymeric chelating agents include, for example, polyethyleneimines, polymethacryloylacetones, poly(acrylic acid), and poly(methacrylic acid). Poly(acrylic acid) is used in some embodiments.

Some suitable metal-complexing agents that are not chelating agents are, for example, alkaline carbonates, such as, for example, sodium carbonate.

Metal-complexing agents may be present in neutral form or in the form of one or more salts. Mixtures of suitable metal-complexing agents are also suitable.

In some relatively wet embodiments, the amount of metal-complexing agent is, based on the total weight of the water, 25% by weight or less; or 10% by weight or less; or 1% by weight or less. Independently, in some relatively wet embodiments, the amount of metal-complexing agent is, based on the total weight of the water, 0.00001% or more; or 0.0001% or more; or 0.01% or more.

Independently, in some relatively wet embodiments, the molar concentration of metal-complexing agent in the water (i.e., moles of metal-complexing agent per liter of water) is 0.00001 mM (i.e., milli-Molar) or greater; or 0.0001 mM or greater; or 0.001 mM or greater; or 0.01 mM or greater; or 0.1 mM or greater. Independently, in some relatively wet embodiments, the concentration of metal-complexing agent is 100 mM or less; or 10 mM or less; or 1 mM or less.

In some relatively dry embodiments, the ratio of the weight of metal complexing agent to the weight of cyclopropene molecular encapsulating agent complex is 0.001 or greater; or 0.003 or greater; or 0.01 or greater; or 0.03 or greater; or 0.1 or greater. Independently, in some relatively dry embodiments, the ratio of the weight of metal complexing agent to the weight of cyclopropene molecular encapsulating agent complex is 1000 or lower; or 300 or lower; or 100 or lower; or 30 or lower; or 10 or lower.

In some embodiments of the present invention, one or more adjuvants is also included in the composition of the present invention. The use of adjuvants is considered optional in the practice of the present invention. Adjuvants may be used alone or in any combination. When more than one adjuvant is used, it is contemplated that any combination of one or more adjuvants may be used. Some suitable adjuvants are surfactants, alcohols, oils, extenders, pigments, fillers, binders, plasticizers, lubricants, wetting agents, spreading agents, dispersing agents, stickers, adhesives, defoamers, thickeners, transport agents, and emulsifying agents.

In some embodiments, a composition of the present invention is used that contains at least one adjuvant selected from alcohols, oils, and mixtures thereof; such a composition may or may not additionally contain one or more surfactant.

In some embodiments, a composition of the present invention may be stored for later use. Compositions of the present invention may be stored in any form (for example, whether or not they are present in a relatively dry embodiment, or, for example, whether or not they are present in a relatively wet embodiment). In some embodiments, the composition of the present invention may be stored in a sealed container. A sealed container is one that is constructed so that no effective amount of material (solid, liquid, or gas) passes in or out of the container. Independent of the type of container used, compositions of the present invention may be stored for 3 hours or longer; or 8 hours or longer; or 1 day or longer; or 1 week or longer; or 3 weeks or longer; or 2 months or longer; or 6 months or longer.

A composition of the present invention may be used in a wide variety of ways. For example, a relatively dry embodiment may be made and then stored for later use. In some embodiments, such a relatively dry embodiment may be mixed with water to make a relatively wet embodiment. It is contemplated that a relatively dry embodiment of the present invention will, in some cases, dissolve and/or disperse in water more readily than a comparable relatively dry composition that had little or no salt.

When a relatively wet embodiment is used, in some cases such an embodiment may be stored until later use. It is contemplated that, in some cases, storage will be in a container that is sealed. In some cases, when such an embodiment is stored in a sealed container, the sealed container has a small headspace or has no headspace. As used herein, "headspace" is the volume of the interior of the sealed container that is not occupied by solid or liquid materials. Headspace is contemplated to be filled with gas, which may be, for example, air, water, cyclopropene, or mixtures thereof. By small headspace, it is meant that the ratio of the volume of the headspace to the volume of the container is, expressed as a percentage, 5% or less. In some embodiments, the ratio of the volume of the headspace to the volume of the container is 2% or less; or 1% or less; or 0.5% or less; or zero.

In some embodiments of the practice of the present invention, a relatively wet embodiment of the composition of the present invention is stored in a sealed container. Among such embodiments are, for example, embodiments in which there is some headspace. It is contemplated that, independent of size of the volume of the headspace, in some embodiments in which there is a headspace, the pressure in the headspace is, at most, atmospheric pressure plus the vapor pressure of the formulation. That is, in some embodiments involving a sealed container, no excess pressure will be applied to the contents of the sealed container; that is, in such embodiments, pumps, pistons, or other means will not be used to bring the pressure inside the sealed container above the pressure that is the sum of atmospheric pressure and the vapor pressure of the formulation.

Among embodiments in which plants are treated using methods involving a composition of the present invention, the plants that are treated may be any plants that produce a useful product. Among embodiments in which plant parts are treated using methods involving a composition of the present invention, the plant parts that are treated may be any part of plants that produce a useful product. In some embodiments, useful plant parts are treated with a method involving use of a composition of the present invention.

As used herein, to "treat" a plant or plant part means to bring the plant or plant part into contact with a material.

In embodiments of the present invention in which a plant or plant part is treated, a composition of the present invention is used in a way that brings cyclopropene into contact with the plant or plant part. In some embodiments, the method involves using a composition of the present invention in a way that releases cyclopropene from the cyclopropene molecular encapsulating agent complex under conditions in which the cyclopropene then comes into contact with the plant or plant part.

For example, a relatively wet embodiment of the composition of the present invention may be used in a process that brings cyclopropene into contact with plants or plant parts. Such contact may be performed in any of a wide variety of ways. For example, a relatively wet embodiment of the composition of the present invention is placed in a closed space (such as, for example, a transportation trailer or a controlled-atmosphere room) along with plants or plant parts, and operations are performed on the composition to promote the release of cyclopropene from the composition into the atmosphere of the closed space. Operations that promote the release of cyclopropene from the composition include, for example, introducing gas bubbles into the composition.

For another example, a relatively dry embodiment of the composition of the present invention may be placed in a closed space along with plants or plant parts, operations may be performed on the composition to promote the release of cyclopropene from the composition into the atmosphere of the closed space. Operations that promote the release of cyclopropene from the composition include, for example, contacting the relatively dry composition of the present invention with water or with a high-humidity atmosphere.

In some embodiments, the practice of the present invention involves bringing the cyclopropene molecular encapsulating agent complex into contact with the plant or plant part. While the present invention is not limited to any particular theory or mechanism, it is contemplated that, in embodiments in which a cyclopropene molecular encapsulating agent complex is brought into contact with a plant or plant part, some or all of the cyclopropene subsequently departs from the molecular encapsulating agent and, possibly after a diffusion process, comes into direct contact with the plant or plant part.

For example, a relatively wet embodiment of the composition of the present invention may be brought into contact with plants or plant parts directly. Some examples of methods of such contact are, for example, spraying, foaming, fogging, pouring, brushing, dipping, similar methods, and combinations thereof. In some embodiments, spraying or dipping or both is used. In some embodiments, spraying is used. Such contact may be performed indoors or outdoors. In some of such embodiments, contact is performed on all or part of a plant while it is growing in a field.

Normally, a specific part of the plant forms the useful product. A plurality of useful plant parts, after removal from a plurality of plants, is known as a "crop." Some types of plants have a single type of useful plant part, while other types of plants have plural types of useful plant parts.

Among the plants and plant parts that are suitable for use in the present invention, are, for example, plants (and parts thereof) with plant parts that are edible, plants (and parts thereof) with plant parts that are non-edible but useful for some other purpose, and combinations thereof. Also contemplated as suitable plants (and parts thereof) are those from which useful materials can be extracted; such useful materials may be, for example, edible materials, raw materials for manufacturing, medicinally useful materials, and materials useful for other purposes.

Further contemplated as suitable plants (and parts thereof) are those that yield plant parts that are useful for their beauty and/or ornamental properties. Such ornamental plant parts include, for example, flowers and other ornamental plant parts such as, for example, ornamental leaves. Some of such plants produce useful bulbs. In some embodiments, an entire ornamental plant is considered to be the useful plant part.

Plants that produce all types of edible plant parts are contemplated as suitable for use in the present invention. Also suitable are all types of edible plant parts.

Many of the plants (and parts thereof) that are suitable for use in the practice of the present invention can be usefully divided into categories or groups. One useful method for defining such groups is the "Definition and Classification of Commodities," published on or before Mar. 23, 2006, by the Food and Agriculture Organization ("FAO") of the United Nations as a "Draft." In the practice of some embodiments of the present invention, it is contemplated to treat plants that produce one or more crops that fall within any of the crop groups defined by the FAO. In some embodiments, it is contemplated to treat one or more crops that fall within one or more of those groups.

It is to be understood that for purposes of the present specification and claims that the range and ratio limits recited herein can be combined. For example, if ranges of 60 to 120 and 80 to 110 are recited for a particular parameter, then the ranges of 60 to 110 and 80 to 120 are also contemplated. For another example, if minimum values for a particular parameter of 1, 2, and 3 are recited, and if maximum values of 4 and 5 are recited for that parameter, then it is also understood that the following ranges are all contemplated: 1 to 4, 1 to 5, 2 to 4, 2 to 5, 3 to 4, and 3 to 5.

EXAMPLES

In the Examples below, "Powder 1" was a dry powder that was a complex of 1-MCP with alpha-cyclodextrin that contains 4.1% 1-MCP by weight, based on the weight of Powder 1. When Powder 1 was slurried in liquid, the concentration is characterized herein as the ratio of weight of Powder 1 (in grams) to the volume of liquid (in milliliters), expressed as a percentage (for example, 0.5 gram of powder 1 in 20 ml of liquid makes a 2.5% slurry). Concentrations of aqueous salt solutions are characterized herein by the ratio of weight of salt to weight of solution, expressed as a percentage.

Example 1

Escape of 1-MCP from 2.5% Aqueous Slurries

The liquid used in the slurries was either deionized water or a salt solution. Each slurry was placed in a glass septum bottle (volume of 122 milliliter), which was then sealed. Then a sample of the headspace gas was removed and tested at each of the times after sealing shown below in Table 1. The headspace gas was analyzed by gas chromatography for the concentration of 1-MCP in the headspace gas, from which the total amount of 1-MCP in the headspace gas was calculated and reported as a percentage of the total 1-MCP in the glass septum bottle.

TABLE 1

Escape of 1-MCP from 2.5% Slurries: % 1-MCP in Headspace

| Example | Liquid | at 1 hour | at 3 hours | at 5 hours |
|---------|--------|-----------|------------|------------|
| 1a-C | water | 8.1% | 12.7% | 14.6% |
| 1b | 40% Ammonium Sulfate | 0.18% | 0.29% | 0.34% |
| 1c | 25% Sodium Sulfate | 0.66% | 1.0% | 1.3% |
| 1d | 25% Disodium Phosphate | 2.7% | 5.1% | 5.6% |
| 1e | 25% Sodium Acetate | 3.0% | 4.4% | 5.1% |
| 1f | 25% Ammonium Chloride | 4.2% | 6.3% | 7.6% |
| 1g | 20% Sodium Chloride | 6.5% | 10.5% | 12.4% |
| 1h-C | 40% Calcium Chloride | 17.5% | 27.7% | 30.2% |

Samples 1a-C and 1h-C are Comparative Examples. Release of 1-MCP from the slurries made with salt solutions of the invention are much lower than release of 1-MCP from slurries 1a-C and 1h-C.

Example 2

Stability of 6.25% Slurries Stored with No Headspace 6.25% slurries were prepared from Powder 1, in deionized water and in 40% ammonium sulfate. Each slurry was placed in a vial (volume 8 milliliter) with no headspace. The vials were stored in the dark at approximately 25° C.

It is known that when such slurries in water are stored, the 1-MCP eventually disappears. It is contemplated that the 1-MCP gradually diffuses out of the complex and then is affected by chemical reaction to become some other compound. In order to study whether this disappearance occurs, after a specified storage time, the slurry is analyzed to determine how much of the initial 1-MCP is still present in the slurry. To do that analysis, the vial was emptied into an evaporating dish in a chamber (volume 36 liter); 20 milliliter of surfactant (Arquad™ C-33, 1% solution, from Akzo-Nobel) was added to cause release of essentially all the 1-MCP from the slurry; the chamber was sealed; and the concentration of 1-MCP in the atmosphere of the chamber was sampled and analyzed by gas chromatography. From the concentration, the total amount of 1-MCP in the atmosphere was calculated. The amount of 1-MCP in the atmosphere is expressed as a percentage of the total 1-MCP that was present in the slurry at the time of formation of the slurry. Thus, for example, a result of 75% 1-MCP means that 25% of the original 1-MCP has disappeared. To study this phenomenon over various storage times, a series of identical slurries are made and then analyzed at different storage times. Analyses performed before storage are shown as "initial." The results are shown below in Table 2.

TABLE 2

Stability of 6.5% Slurries: % 1-MCP in Chamber

| Example | Liquid | initial | 1 week | 2 weeks |
|---------|--------|---------|--------|---------|
| 2a-C | water | 100% | 92% | 75% |
| 2b | 40% ammonium sulfate | 100% | 100% | 92% |

The 6.5% slurry in 40% ammonium sulfate (Example 2b) is more stable than the 6.5% slurry in water (Comparative Example 2a-C).

Example 3

Storage Stability of 25% Slurries

25% slurries were prepared with Powder 1 in various salt solutions. Stability was tested as in Example 2. Results are in Table 3.

TABLE 3

Stability of 25% Slurries: % 1-MCP in Chamber

| Example | Liquid | initial | 3 weeks |
|---------|--------|---------|---------|
| 3a | 40% magnesium sulfate | 100% | 100% |
| 3b | 40% ammonium sulfate | 100% | 100% |
| 3c | 20% ammonium sulfate | 100% | 96% |
| 3d | 10% ammonium sulfate | 100% | 89% |

All of the tested slurries are usefully stable over 3 weeks.

We claim:

1. A composition comprising
   (a) at least one cyclopropene molecular encapsulating agent complex, and
   (b) at least one non-deliquescent salt, wherein no chloride salt is used;
   wherein the ratio of dry weight of said salt to dry weight of said cyclopropene molecular encapsulating agent complex is from 0.03 to 500, and wherein said composition has more than 30% water by weight, based on the weight of said composition, has a ratio of dry weight of said salt to weight of said water of at least 0.3, and has said cyclopropene molecular encapsulating agent complex distributed throughout said water.

2. The composition of claim 1 wherein said non-deliquescent salt comprises magnesium sulfate.

3. The composition of claim 1 wherein at least one said non-deliquescent salt is dissolved in said water.

* * * * *